United States Patent [19]

Brown

[11] Patent Number: 5,792,117
[45] Date of Patent: Aug. 11, 1998

[54] APPARATUS FOR OPTICALLY DETERMINING AND ELECTRONICALLY RECORDING INJECTION DOSES IN SYRINGES

[75] Inventor: Stephen J. Brown, Mountain View, Calif.

[73] Assignee: Raya Systems, Inc., Mountain View, Calif.

[21] Appl. No.: 681,223

[22] Filed: Jul. 22, 1996

Related U.S. Application Data

[63] Continuation-in-part of Ser. No. 278,929, Jul. 22, 1994, Pat. No. 5,569,212.
[51] Int. Cl.[6] .................................................. A61M 5/00
[52] U.S. Cl. ........................ 604/207; 604/246; 235/465; 22/23; 22/30
[58] Field of Search .......................... 604/207–211, 246; 128/DIG. 1; 235/454, 462, 465; 22/23, 30

[56] References Cited

U.S. PATENT DOCUMENTS

| | | |
|---|---|---|
| 4,846,797 | 7/1989 | Howson et al. . |
| 4,853,521 | 8/1989 | Clacys et al. . |
| 4,950,246 | 8/1990 | Muller . |
| 4,978,335 | 12/1990 | Arthur, III . |
| 5,019,974 | 5/1991 | Beckers . |
| 5,176,502 | 1/1993 | Sanderson et al. . |
| 5,569,212 | 10/1996 | Brown . |
| 5,593,390 | 1/1997 | Castellano et al. . |
| 5,628,309 | 5/1997 | Brown . |
| 5,651,775 | 7/1997 | Walker et al. . |

*Primary Examiner*—Mark Bockelman
*Attorney, Agent, or Firm*—Lumen Intellectual Property Services

[57] ABSTRACT

An apparatus for optically determining and electronically recording the dose of an agent delivered with a syringe. The syringe has a barrel for holding the agent and a plunger movably positioned in the barrel for expelling the agent. The barrel has an injection end through which the agent is expelled. The plunger has a variable color marking whose color varies along the direction of the longitudinal axis of the plunger. The color of the variable color marking at a predetermined distance from the injection end of the barrel varies in dependence upon the position of the plunger in the barrel. The apparatus includes an optical measuring instrument for measuring the color of the variable color marking at the predetermined distance from the injection end. A microprocessor determines the dose from the measured color. A recorder, such as a digital memory unit, electronically records the determined dose.

20 Claims, 4 Drawing Sheets

APPARATUS FOR OPTICALLY DETERMINING AND ELECTRONICALLY RECORDING INJECTION DOSES IN SYRINGES

CONTINUATION APPLICATION INFORMATION

This application is a continuation in part of application Ser. No. 08/278,929, now U.S. Pat. No. 5,569,212 filed Jul. 22, 1994. This application is also related to application Ser. No. 08/591,308, filed Jan. 25, 1996, now U.S. Pat. No. 5,628,309. All of the above applications are hereby incorporated by reference.

BACKGROUND

1. Field of the Invention

The present invention relates to the field of injection syringes, and in particular to an apparatus for optically determining and electronically recording the dose of an agent delivered with an injection syringe.

2. Description of Prior Art

In recent years, the value of keeping electronic medical records in place of paper records has been widely recognized in the healthcare industry. The use of electronic medical records allows healthcare providers and patients to store, retrieve, and share medical information with considerably more ease and accuracy. The sharing of medical information is particularly important in treatment programs involving the injection of insulin, human growth hormone, or other medications.

Typically, these injections are performed using disposable syringes. Unfortunately, no adequate apparatus exists that measures and electronically records dose information from a disposable syringe. As a result, the patient or healthcare worker performing the injection is burdened with the task of injecting the dose and then manually recording the dose amount in a log book.

Because of the frequency of such injections, often several times a day for diabetics, it becomes difficult to keep accurate records. Indeed, studies have shown that a patient's own records and recollections are often incomplete and inaccurate. Additionally, a patient may intentionally cheat while making self-recorded entries in an attempt to create a log book that will please his or her doctor. In the long-term this makes patient monitoring extremely difficult and jeopardizes the treatment program, possibly even endangering the patient's life.

Attempts have been made at developing electronic management systems for assisting patients in self-administered drug programs. For example, U.S. Pat. No. 5,019,974 issued to Beckers describes a hand-held, microprocessor-based recorder that interfaces with a master computer. The patient enters therapy information into the recorder via a keyboard. The recorder includes a display for displaying treatment therapy guidelines to the patient. The recorder also has a blood glucose meter for recording the patient's blood glucose levels.

Unfortunately, the recorder described by Beckers does not automatically measure and record dose information from a disposable syringe. After injecting a dose, the patient must manually enter the dose information into the recorder using switches or keys. Although this is an improvement over keeping written records on paper, the effectiveness of the drug program is still limited by the patient's recollections and recordings, which are unreliable.

Attempts have also been made at developing devices that deliver a predetermined dose of medication and record the dose amount. For example, U.S. Pat. No. 5,176,502 issued to Sanderson et al. on Jan. 5, 1993 describes a syringe pump for expelling a preset dose of medication from a syringe. The syringe pump includes a syringe retainer for holding the syringe and a driver for engaging the plunger of the syringe. An electric motor pushes the driver and plunger into the syringe barrel to expel the medication.

The syringe pump further includes a monitoring circuit for monitoring the motion of the driver during the delivery of the medication. The monitoring circuit includes a linear potentiometer having an electrically conductive strip of resistive material. The resistive material is positioned such that it engages an electrical contact of the driver. The position of the electrical contact on the resistive strip varies the voltage of the monitoring circuit, thus indicating the position of the plunger inside the barrel. A microprocessor receives voltage signals from the monitoring circuit and compares the voltage signals to preprogrammed signals to determine if the plunger displacement corresponds to correct displacement for delivering the preset dose. A control mechanism connected to the microprocessor regulates the driver's movement to ensure the preset dose of medication is delivered.

Although the syringe pump described by Sanderson does allow electronic recording of dose information, it is only designed to deliver medication directly into an intravenous line. It is not designed to inject a patient directly nor can it measure and record a dose from a syringe unless the syringe pump pushes the plunger. Consequently, the syringe pump is of little use to a healthcare worker who must inject a patient directly or to an outpatient who must follow a self-injection treatment program.

Another device for injecting a preset dose of medication and for recording the injected dose is disclosed in U.S. Pat. No. 4,950,246 issued to Muller on Aug. 21, 1990. Muller describes a battery-operated injection pen having a pump rod driven by an electric motor. The electric motor is controlled by an electronic control unit that includes a microprocessor with a memory for storing dose information. The injection pen further includes a sensor connected to the control unit for electrically determining the position of the pump rod, and thus the amount of medication injected.

Although the injection pen described by Muller does measure and electronically record dose information, it has several disadvantages that preclude its widespread use. First, the injection pen is an expensive device requiring complicated electronic equipment to deliver and record doses. Second, because the injection pen integrates a syringe and electronic recorder into one device, it is not disposable. The patient must use it repeatedly for each injection, even after the injection pen has been contaminated with blood. Consequently, the injection pen does not provide an inexpensive, convenient, or hygienic solution to patients wishing to measure and electronically record injected dose information.

U.S. Pat. No. 4,853,521 issued to Ronald Claeys on Aug. 1, 1989 presents a programmable, intelligent reader unit which receives and records drug data using hand-held or fixed scanners. The scanners read bar codes in place on syringes, ampules, flow meters, etc. In addition, this intelligent reader allows the user to weigh a syringe before and after injection to determine and record the administered amount of medicine. Dosage data logged in this manner can be displayed or printed out in the form of a record.

While this apparatus comes closest to solving the problem, it involves many complicated steps of weighing syringes, scanning in bar codes, etc. These complex procedures as well as the high cost of the apparatus preclude its widespread use. Additionally, the apparatus cannot be easily carried by the user for recording doses while away from the healthcare facility or home. Thus, no inexpensive apparatus exists for determining and electronically recording dose information from a disposable syringe. Further, no such apparatus exists that is both simple in operation and easily carried by a user.

OBJECTS AND ADVANTAGES OF THE INVENTION

In view of the above, it is an object of the present invention to provide an inexpensive apparatus for optically determining and electronically recording an injection dose delivered from a disposable syringe. It is another object of the invention to provide an apparatus that may be easily operated and carried by a user. A further object of the invention is to suit the apparatus to diabetic patients in particular.

These and other objects and advantages will become more apparent after consideration of the ensuing description and the accompanying drawings.

SUMMARY OF THE INVENTION

The invention presents an apparatus for optically determining and electronically recording the dose of an agent delivered with a syringe. The syringe is of the type having a barrel for holding the agent and a plunger movably positioned in the barrel for expelling the agent. The barrel has an injection end through which the agent is expelled.

The plunger has a variable color marking whose color varies along the direction of the longitudinal axis of the plunger. The color of the variable color marking at a predetermined distance from the injection end of the barrel varies in dependence upon the position of the plunger in the barrel. In one embodiment, the color of the variable color marking varies in brightness. In an alternative embodiment, the color of the variable color marking varies in hue.

The apparatus includes an optical measuring instrument, such as a reflectance photometer, for measuring the color of the variable color marking at the predetermined distance from the injection end. A microprocessor is connected to the optical measuring instrument to determine the dose from the measured color. A recorder, such as a digital memory unit, records the determined dose. The apparatus also includes an input/output port connected to the recorder for transmitting recorded data through the input/output port to a host computer.

DESCRIPTION

Figure 1:
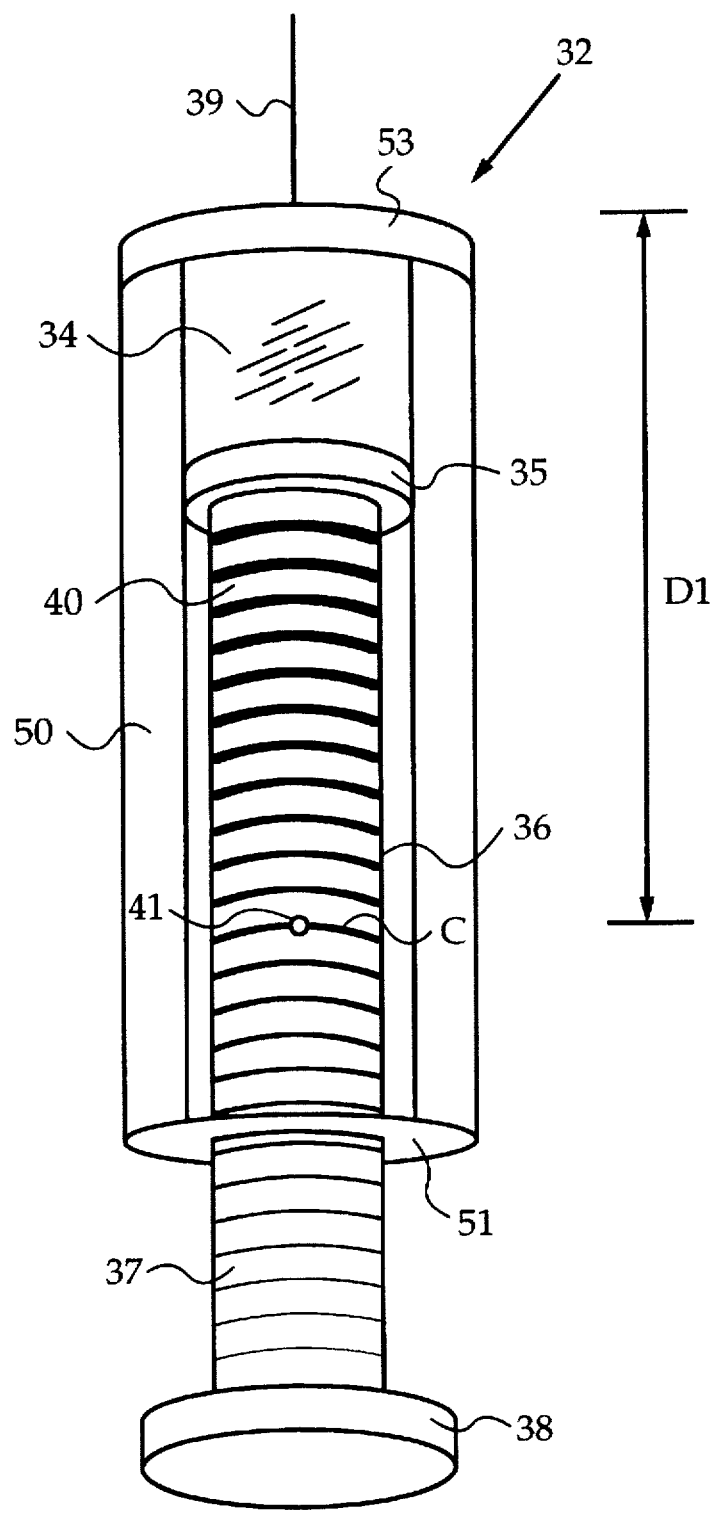
FIG. 1 is a three dimensional, schematic view of a syringe according to the invention.
Figure 2:
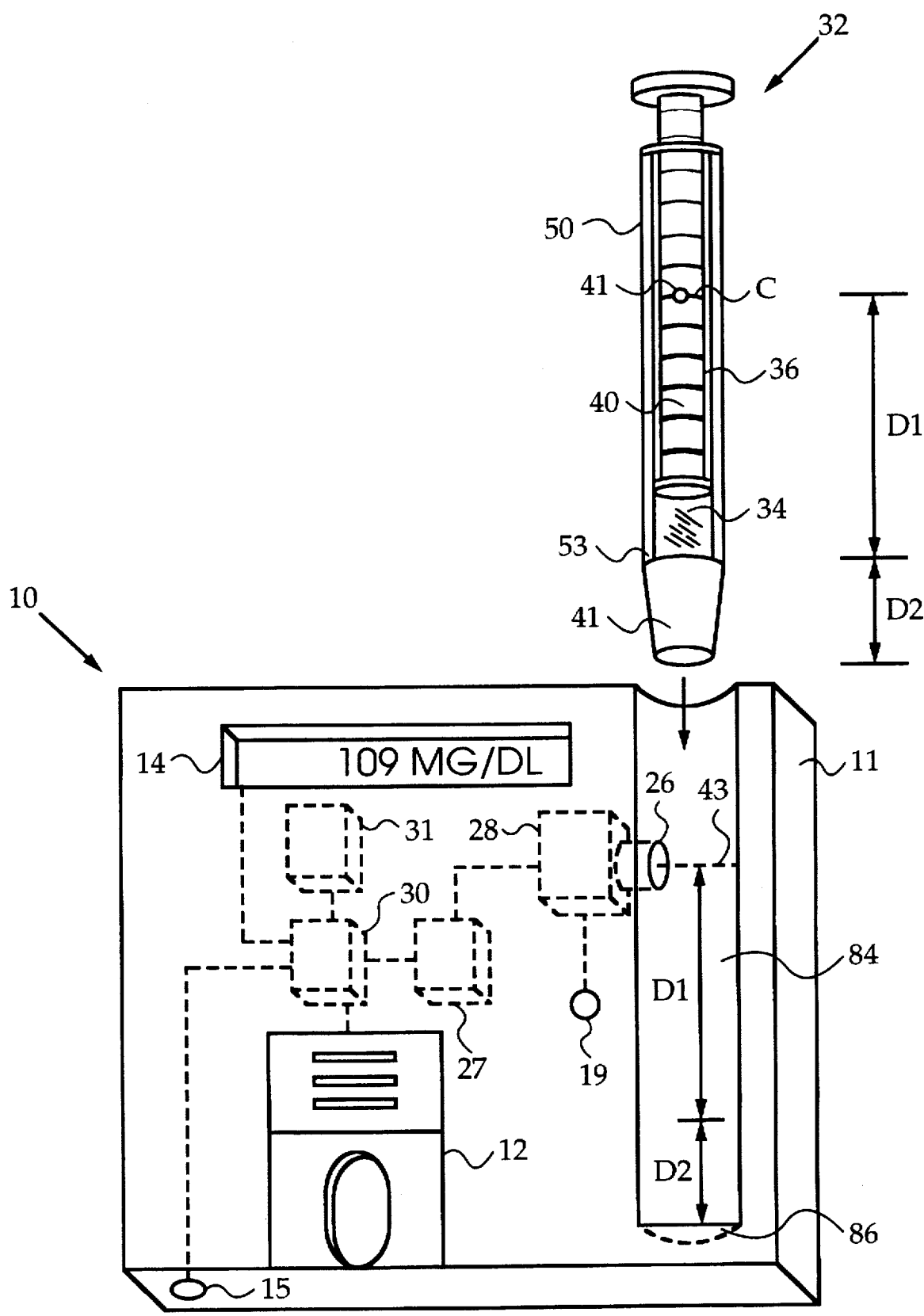
FIG. 2 is a three dimensional, schematic view of the syringe of FIG. 1 being placed in an apparatus for dose measurement.
Figure 3:
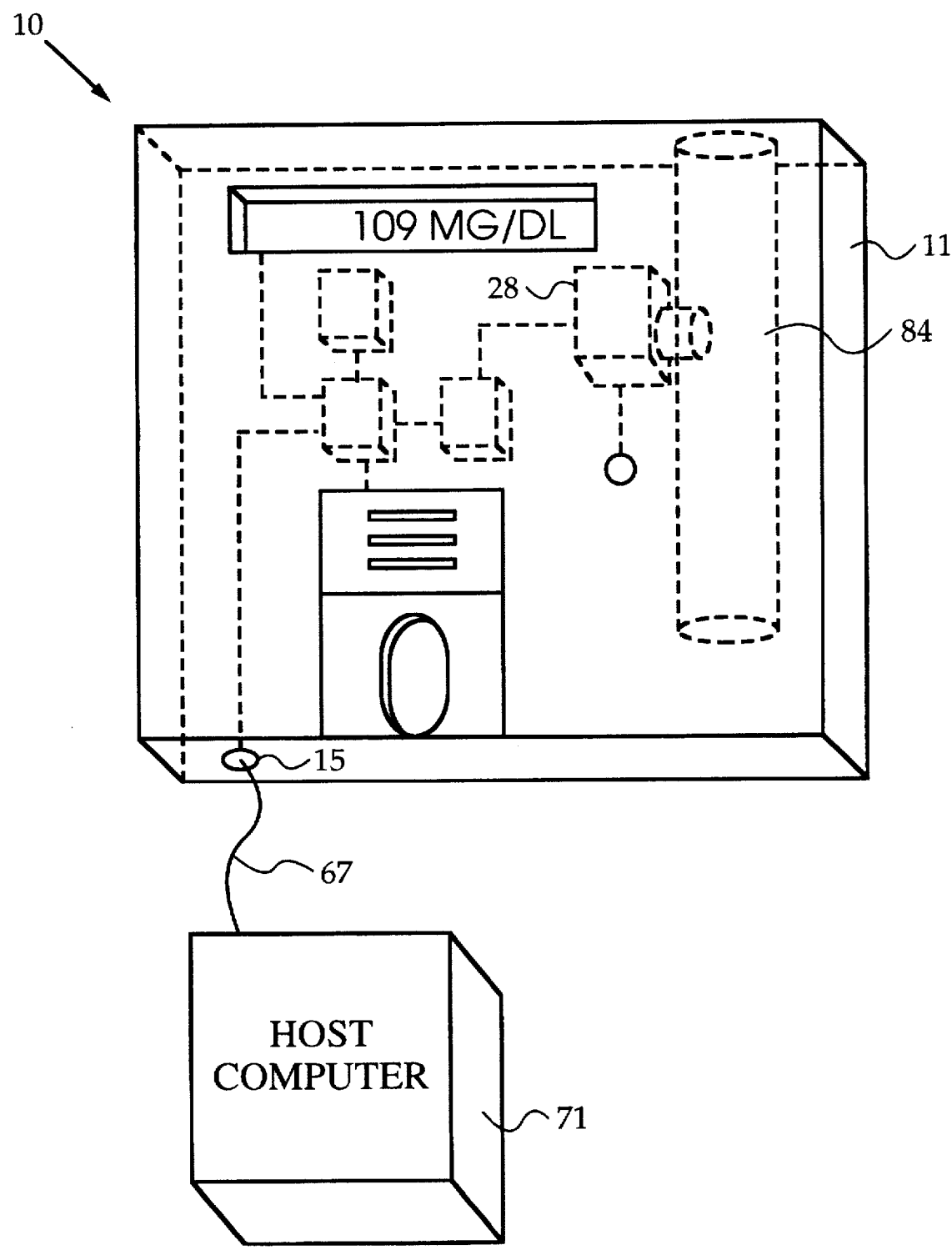
FIG. 3 is a three dimensional, schematic view of another apparatus according to the invention.

A preferred embodiment of the invention is illustrated in FIGS. 1–3. Referring to FIG. 1, a syringe 32 has a barrel 50 for holding a dose of an agent 34. The sides of barrel 50 are substantially transparent such that measurable light may be transmitted through the sides of barrel 50. Barrel 50 has an insertion end 51 and an injection end 53. A plunger 36 having a piston section 35, a plunger rod 37, and a cap 38 is inserted through insertion end 51. A needle 39 is attached to injection end 53 such that needle 39 is in fluid communication with barrel 50. Plunger 36 is movably positioned in barrel 50 for expelling the dose of agent 34 through needle 39. Agent 34 occupies the inner volume of barrel 50 between piston section 35 and injection end 53.

Plunger rod 37 has a variable color marking 40 on its outer surface. Variable color marking 40 extends along the outer surface of rod 37 from piston section 35 to cap 38. The color of marking 40 varies along the direction of the longitudinal axis of rod 37. In the preferred embodiment, the color of marking 40 varies in hue through the visible spectrum. In an alternative embodiment, the color of marking 40 varies in brightness from black to white. Marking 40 is preferably painted or dyed on rod 37. Alternatively, marking 40 may be painted or dyed onto a separate label which is then attached to rod 37.

A color C of marking 40 at a point 41 located a predetermined distance D1 from injection end 53 varies in dependence upon the position of plunger 36 in barrel 50. Distance D1 is selected to be a sufficient distance to ensure that point 41 lies on rod 37 when barrel 50 contains the maximum dose of agent 34 it is designed to hold.

Referring to FIG. 2, an apparatus 10 includes a housing 11 which is sufficiently compact to allow apparatus 10 to be hand-held and carried by a user. Housing 11 has a slot 84 for receiving and aligning syringe 32 for dose measurement. Slot 84 has a bottom 86 and a window 26. In the preferred embodiment, syringe 32 has a needle cover 41 for protecting a user from needle 39 during dose measurement. Needle cover 41 has a length D2. Window 26 and bottom 86 are separated by a distance equal to the sum of distances D1 and D2 so that window 26 is located distance D1 from injection end 53 when syringe 32 is placed in slot 84.

FIG. 3 shows an alternative arrangement of housing 11 and slot 84. In this alternative arrangement, slot 84 is fully contained within housing 11 so that housing 11 surrounds syringe 32 when syringe 32 is inserted into slot 84. The advantage of this arrangement is that syringe 32 may be conveniently stored in apparatus 10 until the user desires to perform an injection.

Referring again to FIG. 2, an optical measuring instrument 28 is positioned within housing 11 adjacent window 26.

Instrument 28 is for measuring color C of marking 40 at distance D1 from injection end 53. Instrument 28 is of the type that measures color C and produces an analog measurement of the color. In the preferred embodiment, instrument 28 is a reflectance photometer. In alternative embodiments, instrument 28 is a light sensor or similar instrument for measuring color C.

Instrument 28 is positioned within housing 11 such that when syringe 32 is placed in slot 84 with cover 41 resting against bottom 86, a line of sight 43 of instrument 28 passes through window 26 and intersects marking 40 at distance D1 from injection end 53. A button 19 for enabling instrument 28 is located on the top surface of housing 11. Button 19 is connected to instrument 28 such that instrument 28 measures color C of marking 40 when button 19 is depressed.

Instrument 28 is connected to an analog to digital converter 27. Converter 27 is for receiving the analog measurements of color C produced by instrument 28 and converting them to digital measurements. A microprocessor 30 is connected to converter 27 such that microprocessor 30 receives the digital measurements from converter 27. Microprocessor 30 is programmed to calculate the dose of agent 34 in barrel 50 from the digital measurements of color C, as will be explained in the operation section below. An electronic memory 31 is connected to microprocessor 30 such that memory 31 records the dose calculated by microprocessor 30. In the preferred embodiment, memory 31 is a digital memory unit.

Apparatus 10 further includes a testing device 12. Device 12 is of the type that tests a physical condition of a user and produces a digital value representative of the physical condition. Device 12 is connected to memory 31 such that memory 31 records the digital value representative of the physical condition. In the preferred embodiment, device 12 is a blood glucose meter and the digital value represents the user's blood glucose level.

A display 14 is recessed in housing 11 and connected to memory 31 through microprocessor 30. Display 14 is for displaying to the user recorded data stored in memory 31. Referring again to FIG. 3, an input/output port 15 is located on the outer surface of housing 11. Port 15 is connected to memory 31 through microprocessor 30 such that recorded data in memory 31 is transmitted through port 15 to a host computer 71 through a data connection cord 67.

A preferred method for using apparatus 10 to determine and record the dose of agent 34 to be delivered with syringe 32 is illustrated in FIGS. 1–3. To determine a blood glucose level, the user places a finger on device 12. Device 12 draws blood from the user's finger, tests the blood, and produces the digital value representative of the user's blood glucose level. This value is recorded in memory 31 and displayed on display 14 as a "blood glucose level" measurement. The user can now use this measurement to determine an appropriate dose of agent 34 to inject.

Before injecting the dose, the user first places syringe 32 in slot 84 so that cover 41 rests against bottom 86. When cover 81 rests on bottom 86, line of sight 43 of instrument 28 intersects marking 40 at point 41 located distance D1 from injection end 53. Next, the user presses button 19 to cause instrument 28 to measure color C of marking 40 at point 41. Color C varies in dependence upon the position of plunger 36 in barrel 50. Because agent 34 occupies the inner volume of barrel 50 between piston section 35 and injection end 53, the position of plunger 36 inside barrel 50 defines the dose of agent 34 in barrel 50. Thus, a measurement of color C indicates the dose of agent 34 in barrel 50.

An analog measurement of color C is performed by instrument 28 and converted to a digital measurement by converter 27. The digital measurement is received by microprocessor 30 from converter 27. Microprocessor 30 calculates the dose of agent 34 from the digital measurement of color C and records the dose in memory 31. Display 14 displays the calculated dose as a "dose selected" measurement. This alerts the user that the injection of the dose may now be performed. After recording a desired number of doses, the user transmits the data recorded in memory 31 through port 15 to host computer 71.

In the preferred embodiment, microprocessor 30 is programmed during the manufacture of apparatus 10 with a table of values for performing the dosage calculation. The table includes a range of possible values of color C, and a corresponding dose volume for each value of color C. Upon receiving a color measurement, microprocessor 30 retrieves the dose volume corresponding to the color measurement from the table. The table of values is created by measuring color C with instrument 28 for various known volumes of agent 34 in barrel 50. The measured color for each known volume is then placed in the table. To create a precise table, at least ten known volumes of agent 34 ranging from a maximum dose to a minimum dose should be measured to determine the corresponding color C of marking 40 at distance D1 from injection end 53.

Of course, many other methods of calculating dose information from measurements of color C are possible. For example, in one alternative embodiment, microprocessor 30 is programmed to calculate doses using a mathematical function derived from the table of values described in the preferred embodiment. Using the known volumes of agent 34 and the corresponding color measurements produced by instrument 28, a graph of dose volume as a function of measured color is created. By interpolating from the known points on the graph, a mathematical function is derived describing the relationship of measured color to dose volume. Microprocessor 30 then uses the derived mathematical function to calculate dose volumes from the measured color. Specific techniques for calibrating an electronic apparatus by interpolating from test measurements are well known in the art.

The advantage of the apparatus described in the preferred embodiment is that it optically measures a dose directly from an injection syringe and digitally records the dose. The user is not burdened with manually entering the dose information into a log. Additionally, the dose information recorded is more accurate than a user's manual records, which have been shown to be unreliable. Because the syringe requires no electronic equipment, it is manufactured very inexpensively and may be disposed of by the user following its use.

Figure 4:
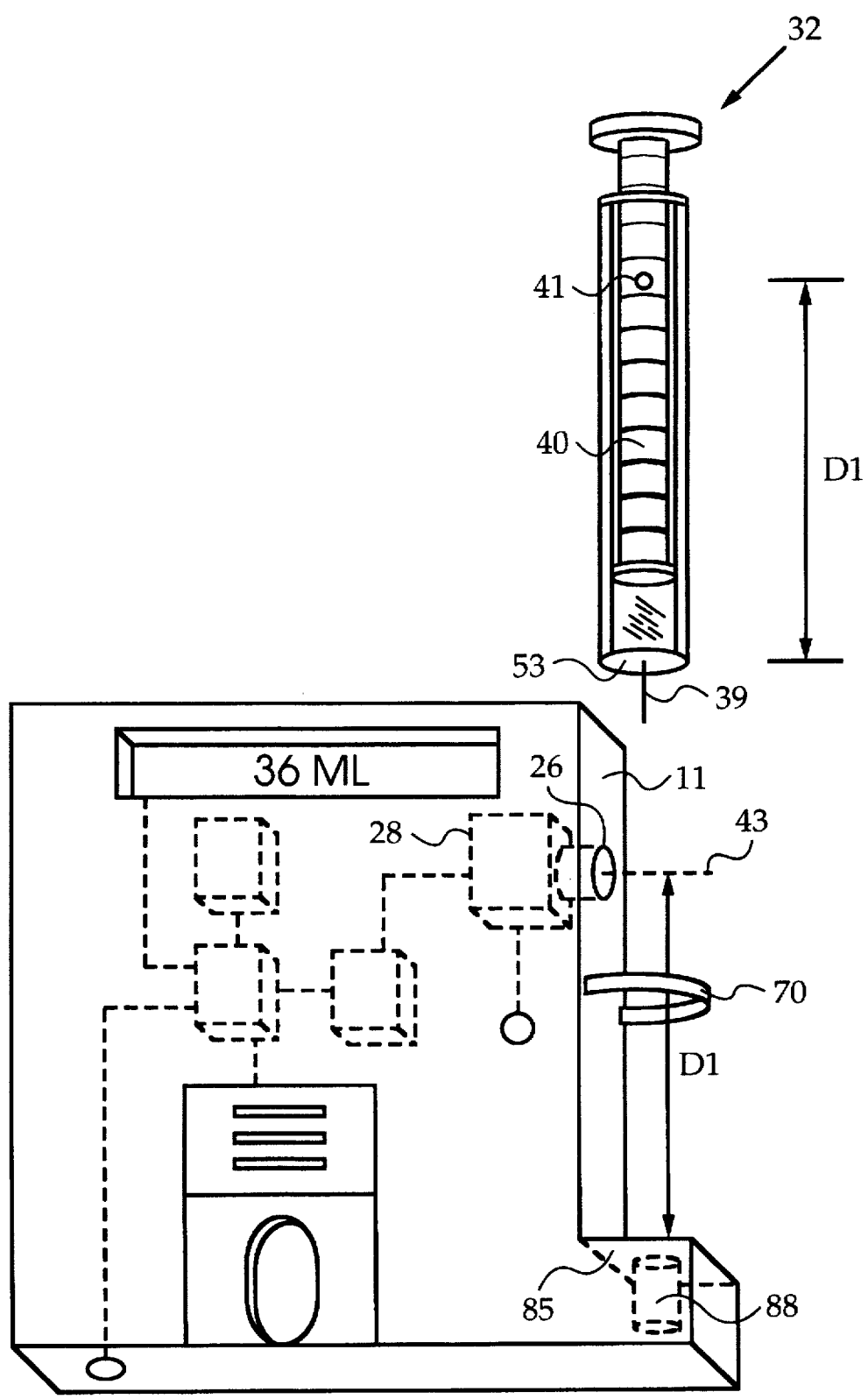
FIG. 4 is a three dimensional, schematic view of the syringe of FIG. 1 being placed in another apparatus for dose measurement.

A second embodiment of the invention is shown in FIG. 4. The second embodiment differs from the preferred embodiment in the design of housing 11. In the second embodiment, housing 11 is designed to receive syringe 32 for dose measurement without needle cover 41. Slot 84 is replaced by a platform 85 and a retaining ring 70 for holding syringe 32. A well 88 for receiving needle 39 is located below platform 85. Well 88 is sufficiently deep to receive the full exposed length of needle 39.

Window 26 and platform 85 are separated by distance D1. Instrument 28 is positioned within housing 11 such that when injection end 53 is placed on platform 85 with barrel 50 retained within retaining ring 70, line of sight 43 of instrument 28 passes through window 26 and intersects marking 40 at distance D1 from injection end 53.

The operation of the second embodiment is similar to the operation of the prefer red embodiment. The primary difference is that syringe 32 is placed in apparatus 10 for dose measurement with needle 39 exposed rather than covered by cover 41. The advantage of the second embodiment is that the user does not have to take the extra step of covering needle 39 before measuring a dose. Other than the differences described, the operation and advantages of this second embodiment are the same as those described in the preferred embodiment above.

SUMMARY, RAMIFICATIONS, AND SCOPE

Although the above description includes many specificities, these should not be construed as limitations on the scope of the invention, but merely as illustrations of the presently preferred embodiment. Many other embodiments of the invention are possible. For example, in one alternative embodiment, the well for receiving the syringe needle contains a supply of agent so that the user may fill the syringe and record the dose at the same time. This embodiment is particularly advantageous for users who perform a high volume of injections, such as hospital workers or other healthcare providers.

Additionally, the apparatus is not limited to the slots and retaining ring illustrated for aligning the syringe with the optical measuring instrument. Any mechanism for holding the syringe in a predetermined position for dose measurement may be used without departing from the scope of the invention. Further, a user could simply hold the optical measuring instrument next to the syringe for dose measurement, so that no alignment system is necessary.

Furthermore, the apparatus is not limited to measuring and recording doses from only one size syringe. In another embodiment, the apparatus includes a microprocessor which is programmed to calculate doses from syringes of different sizes. The microprocessor is connected to a user interface through which the user enters the size of the syringe he or she is using. In this embodiment, the alignment system is also adjustable for aligning syringes of different sizes. Moreover, the apparatus is not limited to aiding a self-care diabetes program. It may be used to aid in the administration of any treatment plan that requires injections.

Therefore, the scope of the invention should be determined not by the examples given but by the appended claims and their legal equivalents.

I claim:

1. In combination with a syringe, an apparatus for determining and recording a dose of an agent delivered with said syringe, said syringe being of the type comprising:
   a) a barrel for holding said agent, said barrel having an injection end;
   b) a plunger movably positioned in said barrel for expelling said agent, said plunger having a variable color marking whose color varies along the direction of the longitudinal axis of said plunger such that the color of said variable color marking at a predetermined distance from said injection end varies in dependence upon the position of said plunger in said barrel;

said apparatus comprising:
   a) an optical measuring means for measuring the color of said variable color marking at said predetermined distance from said injection end;
   b) a circuit means connected to said optical measuring means for determining said dose from the measured color; and
   c) a recording means connected to said circuit means for recording said dose; and
   d) alignment means for aligning the syringe with the optical measuring means, said alignment means having a well-like portion retaining the syringe injection end such that fluids may cannot pass therethrough.

2. The combination syringe and apparatus of claim 1, further comprising an input/output port connected to said recording means for transmitting recorded data from said recording means to a host computer.

3. The combination syringe and apparatus of claim 1, further comprising a testing means for testing a physical condition of a user and for producing a digital value representative of said physical condition, said testing means being connected to said recording means such that said recording means records said digital value representative of said physical condition.

4. The combination syringe and apparatus of claim 3, wherein said testing means comprises a blood glucose meter and said physical condition comprises a blood glucose level.

5. The combination syringe and apparatus of claim 1, further comprising a display connected to said recording means for displaying recorded data.

6. The combination syringe and apparatus of claim 1, further comprising an alignment means for aligning said syringe with said optical measuring means.

7. The combination syringe and apparatus of claim 6, wherein said alignment means comprises a housing having a slot for receiving said syringe, said optical measuring means being positioned within said housing such that when said syringe is placed in said slot, a line of sight of said optical measuring means intersects said variable color marking at said predetermined distance from said injection end.

8. The combination syringe and apparatus of claim 6, wherein said alignment means comprises a housing having a platform and a retaining ring for holding said syringe, said optical measuring means being positioned within said housing such that when said syringe is placed on said platform within said retaining ring, a line of sight of said optical measuring means intersects said variable color marking at said predetermined distance from said injection end.

9. The combination syringe and apparatus of claim 1, wherein the color of said variable color marking varies in brightness.

10. The combination syringe and apparatus of claim 1, wherein the color of said variable color marking varies in hue.

11. The combination syringe and apparatus of claim 1, wherein said optical measuring means comprises a reflectance photometer.

12. The combination syringe and apparatus of claim 1, wherein said recording means comprise a digital memory unit.

13. A method for determining and recording a dose of an agent delivered with a syringe, said syringe being of the type comprising:
   a) a barrel for holding said agent, said barrel having an injection end; and
   b) a plunger movably positioned in said barrel for expelling said agent;

said method comprising the following steps:
   a) placing on said plunger a variable color marking whose color varies along the direction of the longitudinal axis of said plunger such that the color of said variable color marking at a predetermined distance from said injection end varies in dependence upon the position of said plunger in said barrel;
   b) using a syringe holder with optical measuring means, optically measuring the color of said variable color marking at said predetermined distance from said injection end;
   c) determining from the measured color said dose; and
   d) recording said dose in an electronic memory;
   e) removing the syringe from the holder and administering the dosage to a patient;
   f) placing the syringe back in the syringe holder and repeating steps b)–d).

14. The method of claim 13, further comprising the step of transmitting recorded data from said electronic memory to a host computer.

15. The method of claim 13, further comprising the steps of testing a physical condition of a user, producing a digital value representative of said physical condition, and recording said digital value representative of said physical condition in said electronic memory.

16. The method of claim 13, further comprising the step of displaying recorded data stored in said electronic memory on a display.

17. The method of claim 13, wherein the step of optically measuring the color of said variable color marking is performed using a reflectance photometer.

18. The method of claim 17, further comprising the step of aligning said syringe with said reflectance photometer such that a line of sight of said reflectance photometer intersects said variable color marking at said predetermined distance from said injection end.

19. The method of claim 13, wherein the color of said variable color marking varies in brightness.

20. The method of claim 13, wherein the color of said variable color marking varies in hue.

* * * * *